US008884256B2

(12) United States Patent
Sugahara et al.

(10) Patent No.: US 8,884,256 B2
(45) Date of Patent: Nov. 11, 2014

(54) SEPTUM MAGNET AND PARTICLE BEAM THERAPY SYSTEM

(75) Inventors: Kengo Sugahara, Tokyo (JP); Katsuhisa Yoshida, Tokyo (JP); Toshihiro Otani, Tokyo (JP); Shinichi Masuno, Tokyo (JP); Fumihiko Kashima, Tokyo (JP)

(73) Assignee: Mitsubishi Electric Corporation, Chiyoda-Ku, Tokyo (JP)

(*) Notice: Subject to any disclaimer, the term of this patent is extended or adjusted under 35 U.S.C. 154(b) by 0 days.

(21) Appl. No.: 13/576,597

(22) PCT Filed: Feb. 13, 2012

(86) PCT No.: PCT/JP2012/053240
§ 371 (c)(1),
(2), (4) Date: Aug. 1, 2012

(87) PCT Pub. No.: WO2013/121503
PCT Pub. Date: Aug. 22, 2013

(65) Prior Publication Data
US 2013/0207001 A1 Aug. 15, 2013

(51) Int. Cl.
*H05H 7/00* (2006.01)
*H05H 7/04* (2006.01)
*H05H 7/08* (2006.01)

(52) U.S. Cl.
USPC ........ 250/492.3; 315/503; 315/507; 315/501; 250/396 ML

(58) Field of Classification Search
USPC ........... 335/210, 213, 296; 250/396 ML, 398, 250/492.3
See application file for complete search history.

(56) References Cited

U.S. PATENT DOCUMENTS 4,707,676 A * 11/1987 Saitou et al. .................. 335/216
4,737,727 A * 4/1988 Yamada et al. ............... 315/503
(Continued)

FOREIGN PATENT DOCUMENTS

JP 62-143400 6/1987
JP 63-224230 A 9/1988
(Continued)

OTHER PUBLICATIONS

B.Balhan, P. Bobbio, J.Borburgh, E. Carlier, M. Crescenti, M. Hourican, T. Masson, T. Mueller, A. Prost Design and Construction of the LEIR Injection Septa Jun. 2005, European Organization for Nuclear Research.*

(Continued)

*Primary Examiner* — Jack Berman
*Assistant Examiner* — Kevin Chung
(74) *Attorney, Agent, or Firm* — Buchanan Ingersoll & Rooney PC

(57) ABSTRACT

A septum magnet includes a yoke that can be separated at the approximately center portion thereof in the axis direction; a septum coil; a return coil; and a vacuum duct that is inserted between the septum coil and the return coil. The septum coil is formed in such a way as to be able to be separated into a first portion and a second portion in response to separation of the yoke; and in a space between the septum coil and the vacuum duct, there is provided an auxiliary coil, in two portions of which, corresponding to the first portion and the second portion of the septum coil, electric currents flow in opposite direction to each other in a circumferential direction.

5 Claims, 7 Drawing Sheets

(56) References Cited

U.S. PATENT DOCUMENTS

| | | | | |
|---|---|---|---|---|
| 4,783,634 | A | * | 11/1988 | Yamamoto et al. ............ 315/503 |
| 4,931,744 | A | * | 6/1990 | Sonobe et al. ................. 315/503 |
| 5,117,194 | A | | 5/1992 | Nakanishi et al. |
| 5,278,533 | A | * | 1/1994 | Kawaguchi ................... 335/213 |
| 5,483,129 | A | * | 1/1996 | Yamamoto ................... 315/503 |
| 5,576,602 | A | * | 11/1996 | Hiramoto et al. ............. 315/507 |
| 5,587,632 | A | * | 12/1996 | Sakai ............................ 315/507 |
| 5,913,872 | A | * | 6/1999 | Suh et al. ...................... 606/201 |
| 2010/0207552 | A1 | * | 8/2010 | Balakin ......................... 315/503 |

FOREIGN PATENT DOCUMENTS

| | | |
|---|---|---|
| JP | 1-209700 A | 8/1989 |
| JP | 2-174099 A | 7/1990 |
| JP | 6-151096 A | 5/1994 |
| JP | 2001-23798 A | 1/2001 |
| JP | 2001-43998 A | 2/2001 |
| JP | 2002-8899 A | 1/2002 |

OTHER PUBLICATIONS

International Search Report (PCT/ISA/210) issued on Mar. 6, 2012, by the Japanese Patent Office as the International Searching Authority for International Application No. PCT/JP2012/053240.

Written Opinion (PCT/ISA/237) issued on Mar. 6, 2012, by the Japanese Patent Office as the International Searching Authority for International Application No. PCT/JP2012/053240.

* cited by examiner

SEPTUM MAGNET AND PARTICLE BEAM THERAPY SYSTEM

TECHNICAL FIELD

The present invention relates to a septum magnet that is provided in a radiation source such as a circular particle accelerator or a storage ring apparatus and is utilized for supplying or extracting a particle beam.

BACKGROUND ART

A septum magnet is an apparatus that generates a magnetic field in the duct, which is provided in such a way as to share a tangential line with a circulation orbit for a particle beam, for the purpose of making a particle beam in a duct move onto the circulation orbit or making a particle beam existing on the circulation orbit be taken into the duct. In a basic septum magnet, in a gap of a yoke that has a C-shaped cross section, whose opening is oriented to the outer circumference thereof, and that extends in the shape of an arc, a duct that extends in the shape of an arc is disposed in such a way as to be inserted between a septum coil at the outer circumference thereof and a return coil at the inner circumference thereof. The septum coil and the return coil are connected in series with each other in such a way that currents having the same intensity but the opposite directions flow in the circumferential direction. As a result, a magnetic field perpendicular to the circumferential direction, which is the traveling direction of a particle beam, and perpendicular to the radial direction, is generated in the duct, so that the particle beam can be deflected in the radial direction.

Although referred to as coils, the septum coil and the return coil are each formed of copper pipes that are coupled end to end so as to become coil-shaped, because they need to be cooled; therefore, unlike a typical winding coil, they have a high rigidity. Because strong force is exerted on the coil thereof during its operation, the septum magnet is configured, for the convenience of maintenance, in such a way that the yoke thereof can be separated upward and downward in the axis direction, i.e., in the vertical direction at a time when the septum magnet is installed. In this situation, each of the septum coil and the return coil, which have a high rigidity, needs to be separated upward and downward along with the yoke. In this case, the upper coil and the lower coil needs to be separately positioned in such a way that the upper septum and return coils are fixed to the upper yoke and the lower septum and return coils are fixed to the lower yoke. Thus, when the positions of the upper coil and the lower coil differ from each other in the radial direction, an unnecessary radial-direction magnetic field (a skewed magnetic field) is generated.

Accordingly, for example, it is conceivable that a skewed magnetic field is suppressed by use of a technology in which an auxiliary coil is provided in the vicinity of the region where the distribution of the magnetic field needs to be improved (e.g., refer to Patent Documents 1 through 4).

PRIOR ART REFERENCE

Patent Document

[Patent Document 1] Japanese Patent Application Laid-Open No. S63-224230 (Page 3, and FIGS. 1 through 3)
[Patent Document 2] Japanese Patent Application Laid-Open No. H01-209700 (Page 2, and FIGS. 1 and 2)
[Patent Document 3] Japanese Patent Application Laid-Open No. 1106-151096 (Paragraphs 0011 through 0021, and FIGS. 1 through 6)
[Patent Document 4] Japanese Patent Application Laid-Open No. 2001-43998 (Paragraphs 0010 through 0021, and FIGS. 1 through 3)

DISCLOSURE OF THE INVENTION

Problems to be Solved by the Invention

However, in the disclosed technology, the arrangement of auxiliary coils and the magnitude of a current are controlled for the purpose of improving the magnetic-field distribution on a predetermined line out of a cross section perpendicular to the traveling direction of a particle beam; therefore, it is difficult to improve the magnetic-field distribution in the cross section. Accordingly, even when the disclosed technology is applied to a septum magnet where particle beams are widely distributed in a cross section, a region is remained in which an unnecessary magnetic field is not suppressed; thus, the orbit of a particle beam that travels through the region cannot accurately be controlled. Therefore, it has been difficult to utilize a septum magnet, the maintenance of which can readily be performed and with which the orbit of a particle beam can accurately be controlled, in an apparatus, such as a particle beam therapy system, that requires accurate control of a particle beam.

The present invention has been implemented in order to solve the foregoing problems; the objective thereof is to obtain a septum magnet and a particle beam therapy system, the maintenance of which can readily be performed and with which the orbit of a particle beam can accurately be controlled.

Means for Solving the Problems

A septum magnet is characterized by including a yoke that is arc-shaped, that has a gap portion opening at the outer circumference side thereof and extending in a circumferential direction thereof, and that can be separated at the approximately center portion thereof in the axis direction; a septum coil that is provided inside the gap portion but at the outer side thereof in the radial direction and in which, an electric current flows in one direction in the circumferential direction; a return coil that is provided in such a way as to be at the inner side of the gap portion in the radial direction and to face the septum coil with a predetermined distance, and in which an electric current flows in opposite direction to that of the electric current in the septum coil; and a vacuum duct that is inserted between the septum coil and the return coil. The septum magnet is also characterized in that the septum coil is formed in such a way as to be able to be separated into a first portion and a second portion in response to separation of the yoke and in a space between the septum coil and the vacuum duct, there is provided an auxiliary coil, in two portions of which, corresponding to the first portion and the second portion of the septum coil, electric currents flow in opposite direction to each other in the circumferential direction.

Advantage of the Invention

In the septum magnet according to the present invention, an auxiliary coil is provided between the septum coil and the vacuum duct, in two portions of which, corresponding to the portions of the septum coil that is separated along with the yoke, electric currents having directions opposite to each other flow; therefore, by efficiently suppressing a skewed magnetic field caused by a positional difference in the septum coil, a septum magnet and a particle beam therapy system can be obtained which enable maintenance thereof to be readily performed and which can accurately control the orbit of a particle beam.

BEST MODE FOR CARRYING OUT THE INVENTION

Embodiment 1

Figure 1:
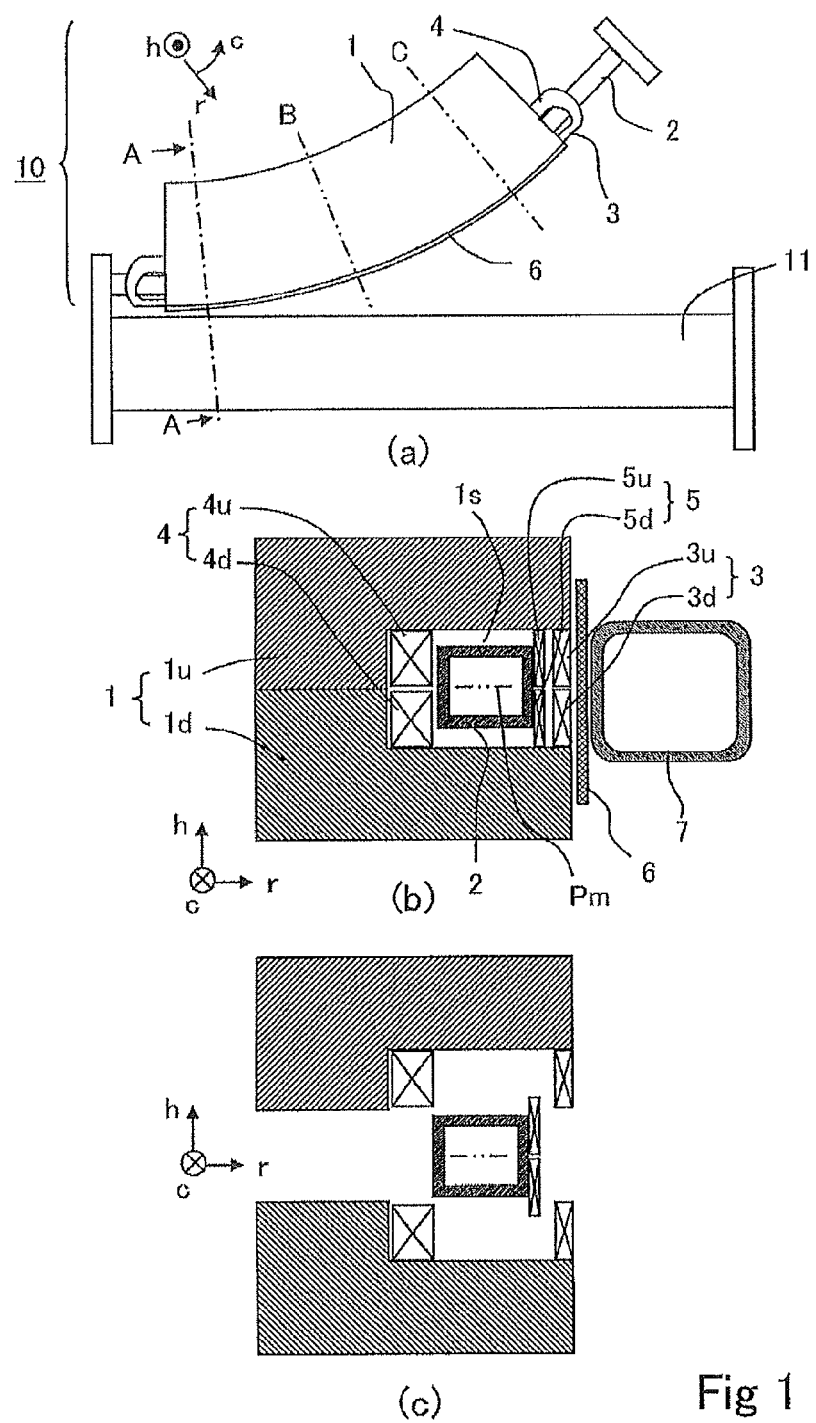
FIG. 1 is a set of plan view and cross-sectional view for explaining the configuration of a septum magnet according to Embodiment 1 of the present invention, and FIG. 1 also includes another cross-sectional view illustrating parts that can be separated when maintenance is performed.
Figure 2:
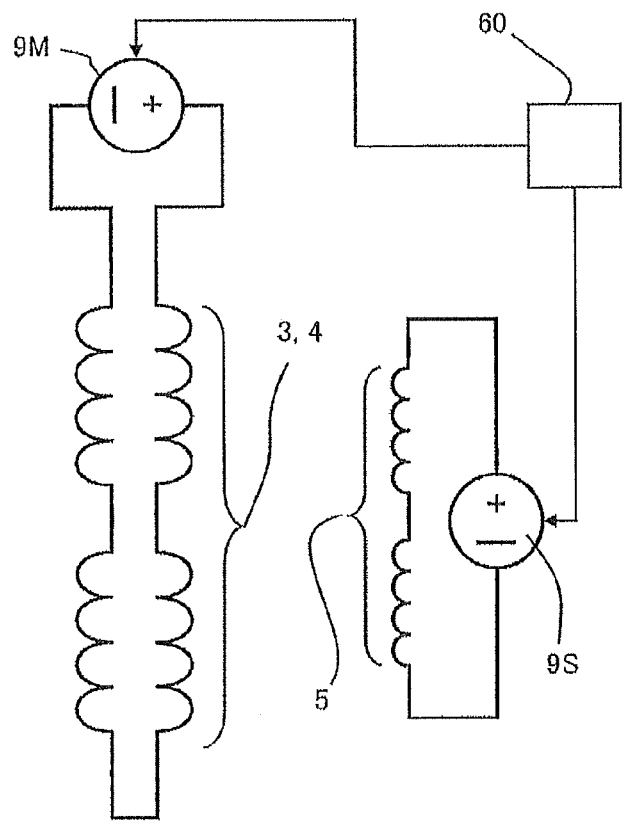
FIG. 2 is a wiring diagram, of coils and driving power sources, for explaining the configuration of a septum magnet according to Embodiment 1 of the present invention.
Figure 3:
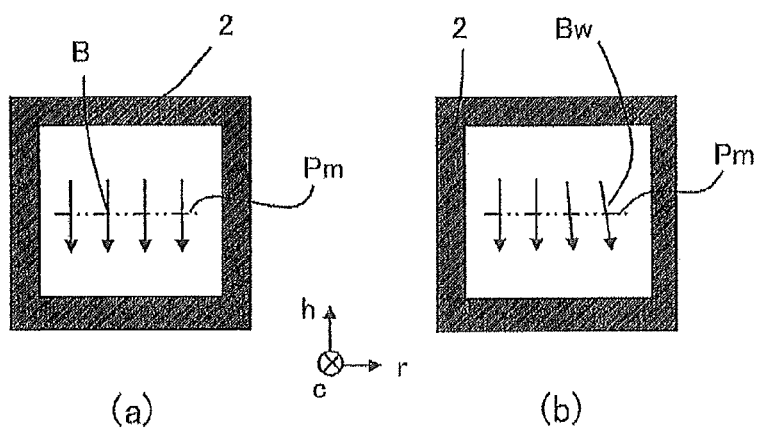
FIG. 3 is a set of schematic cross-sectional views for explaining the operation of a septum magnet according to Embodiment 1 of the present invention and for illustrating magnetic-field components in a plane perpendicular to the orbit of a particle beam inside a vacuum duct.
Figure 4:
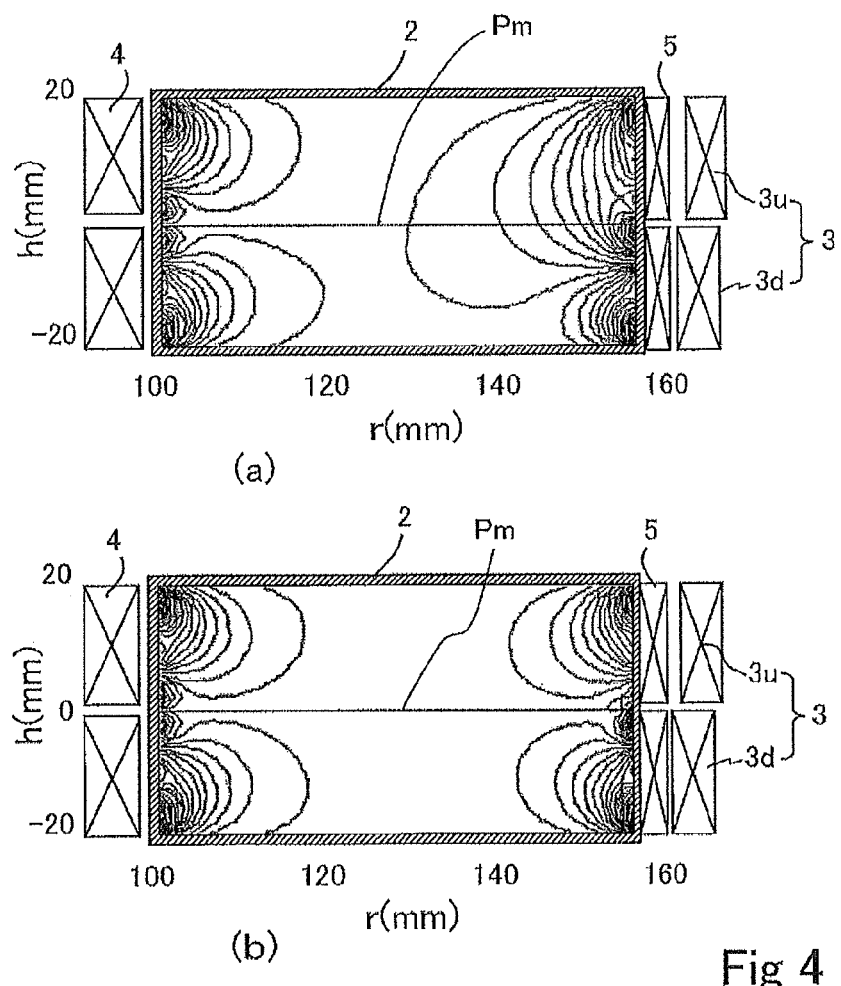
FIG. 4 is a set of schematic cross-sectional views for explaining the operation of a septum magnet according to Embodiment 1 of the present invention and for illustrating magnetic-field distributions in a plane perpendicular to the orbit of a particle beam inside a vacuum duct.
Figure 5:
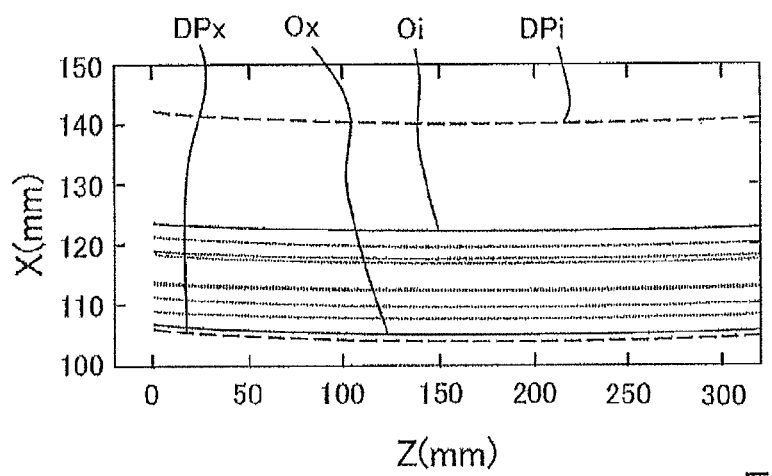
FIG. 5 is a schematic cross-sectional view for explaining the operation of a septum magnet according to Embodiment 1 of the present invention and for representing the orbit of a particle beam inside a vacuum duct.

The configurations and operations of a septum magnet according to Embodiment 1 of the present invention and a particle beam therapy system utilizing the septum magnet will be explained below. FIGS. 1 through 9 are views, diagrams, and flowcharts for explaining the configuration and the operation of a septum magnet according to Embodiment 1 of the present invention and the configuration of a particle beam therapy system utilizing the septum magnet. In FIGS. 1(a) through 1(c), FIG. 1(a) is a side view illustrating the configuration of a septum magnet; FIG. 1(b) is a cross-sectional view in which the depth-direction view in the cross sectional view taken along the A-A line in the side view is omitted; FIG. 1(c) is a cross-sectional view, corresponding to FIG. 1(b), for illustrating the respective relationships between the coils, among main parts of the septum magnet, that are separated from each other when maintenance is performed. FIG. 2 is a wiring diagram illustrating coils included in a septum magnet and driving power sources therefor; FIG. 3 is a set of schematic cross-sectional views illustrating mag- netic-field components in a plane perpendicular to a direction, which is perpendicular to the radial direction and the height direction, i.e., in a plane perpendicular to the orbit of a particle beam in a vacuum duct. FIGS. 4(a) and 4(b) each represent a magnetic-field distribution in a plane perpendicular to the orbit of a particle beam in a vacuum duct at a time when the positions of the upper and lower septum magnets differs from each other; FIG. 4(a) represents the magnetic-field distribution at a time when auxiliary coils are not operated; FIG. 4(b) represents the magnetic-field distribution at a time when the auxiliary coils are operated. FIG. 5 is a schematic circumferential-direction cross-sectional chart representing the orbit of a particle beam in a vacuum duct. FIGS. 1(b), 1(c), 3 and 4 are represented by a cylindrical coordinate system (r, h, c (corresponding to a moving coordinate system in which an orthogonal coordinate system is moved in the circumferential direction)) consisting of the radial-direction position, the axis-direction height, and the circumferential-direction position; FIG. 5 is represented by an orthogonal coordinate system (X, Y, X (a static coordinate system)).

Figure 6:
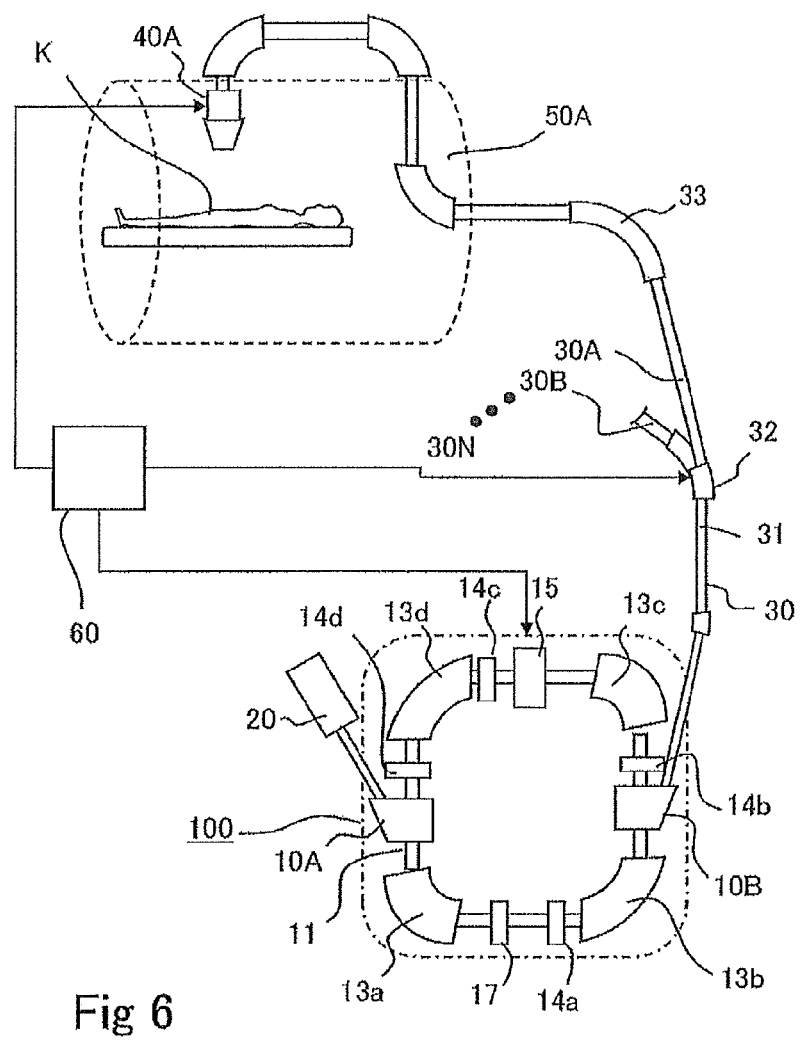
FIG. 6 is a diagram illustrating the configuration of a particle beam therapy system utilizing a septum magnet according to Embodiment 1 of the present invention.
Figure 7:
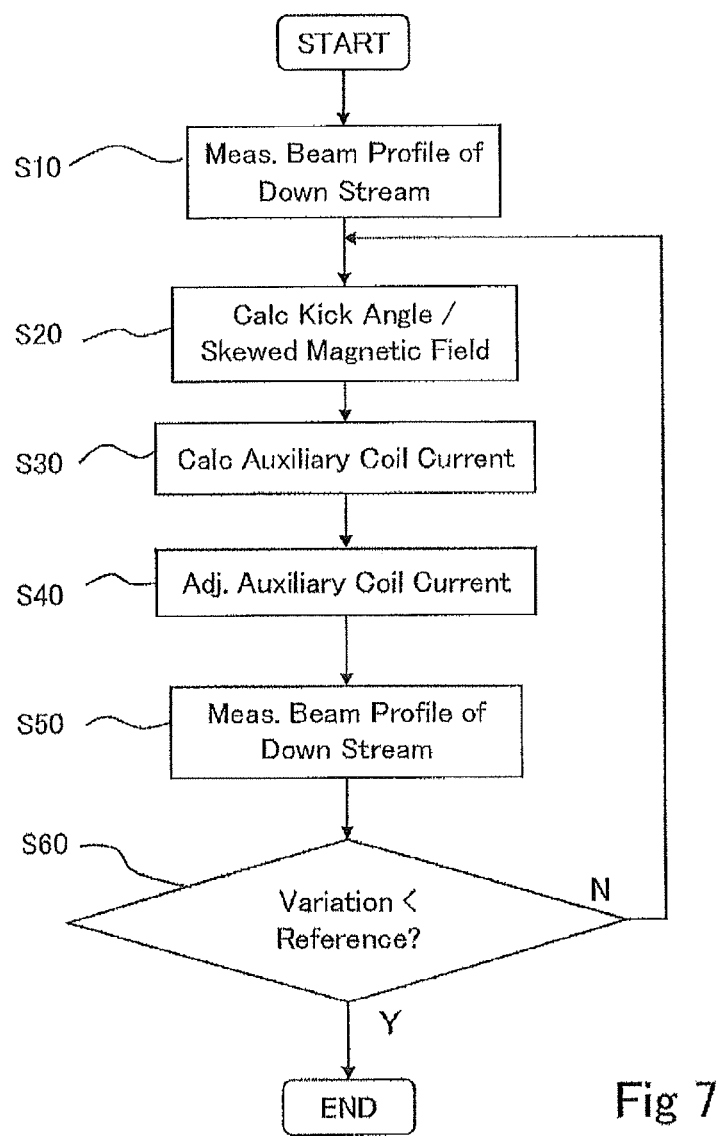
FIG. 7 is a flowchart for explaining a first control method for a septum magnet according to Embodiment 1 of the present invention.
Figure 8:
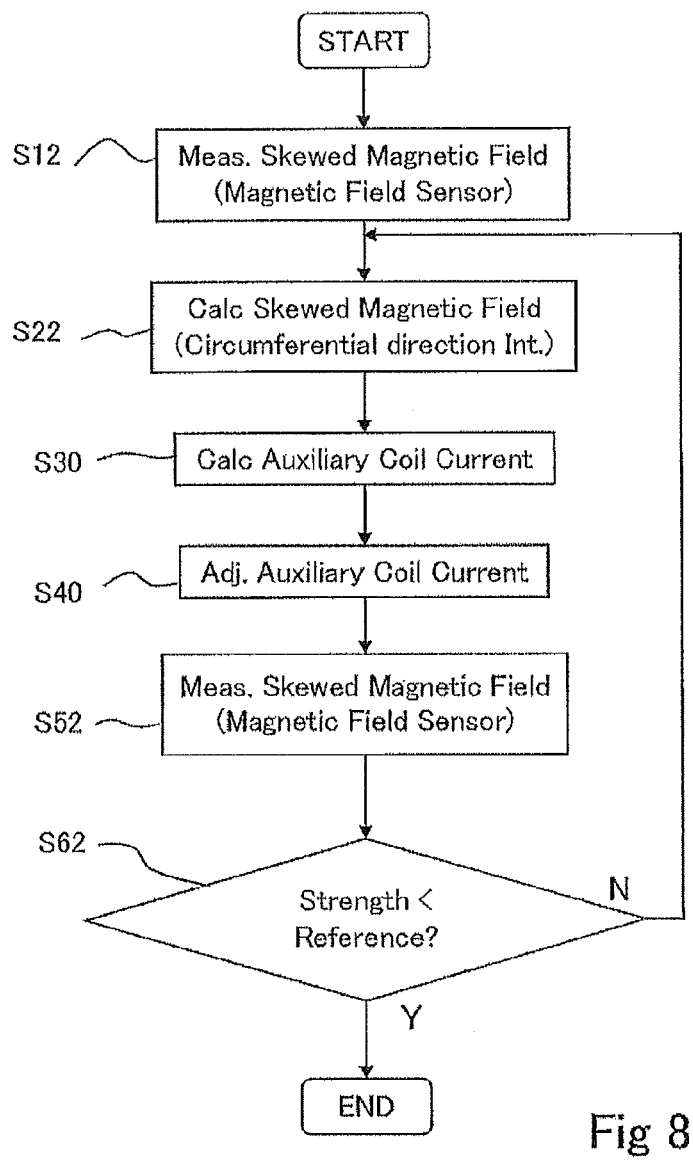
FIG. 8 is a flowchart for explaining a second control method for a septum magnet according to Embodiment 1 of the present invention.
Figure 9:
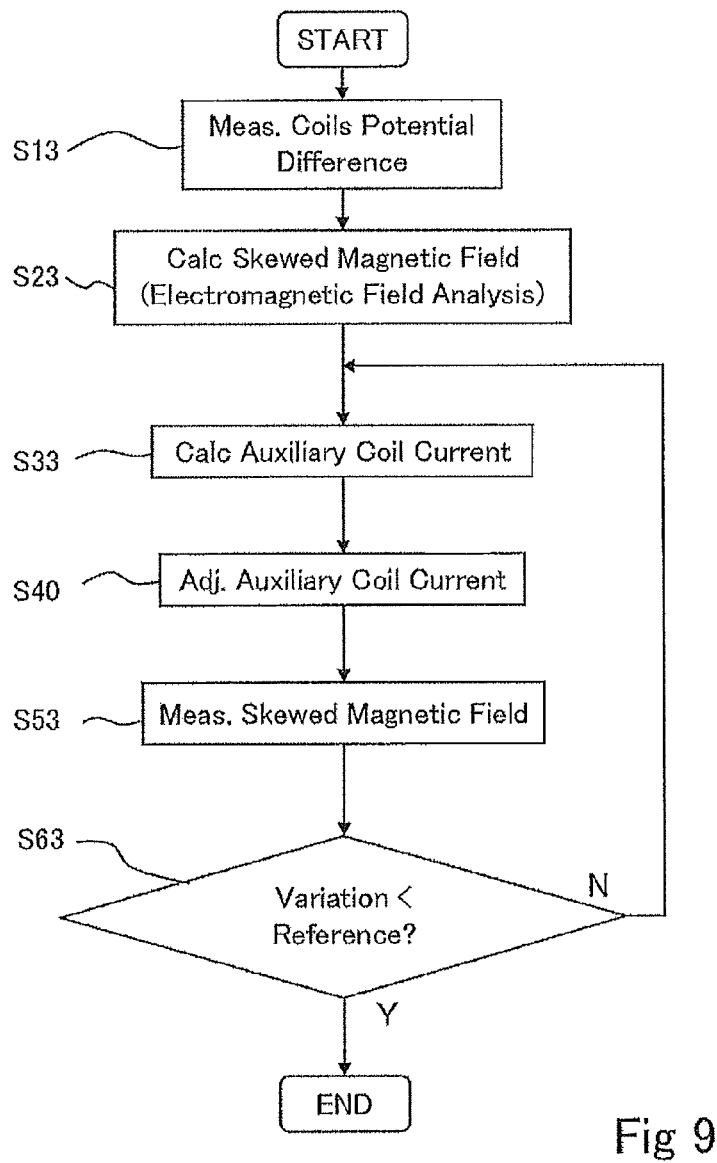
FIG. 9 is a flowchart for explaining a third control method for a septum magnet according to Embodiment 1 of the present invention.

FIG. 6 is a diagram illustrating the configuration of a particle beam therapy system utilizing a septum magnet according to Embodiment 1 of the present invention. FIGS. 7 through 9 are flowcharts for explaining first through third control methods, respectively, for adjusting the current values of auxiliary coils, as control methods for a septum magnet according to Embodiment 1 of the present invention.

At first, based on FIGS. 1 and 2, the configuration of a septum magnet according to Embodiment 1 will be explained.

A septum magnet 10 is arc-shaped and is disposed in such a way as to share a tangential line with a duct 11 included in a circular accelerator 100, described later, or in the circular orbit path of a storage ring; the septum magnet 10 is provided with a yoke 1, whose cross section (r-h plane) perpendicular to the extending direction becomes C-shaped, as illustrated in FIG. 1(b), by providing a gap portion 1s the cross section of that is approximately rectangular and that opens at the outer circumferential side of the yoke, and that extends in the circumferential direction (c); a magnetic shield 6 provided alongside the outer circumferential side of the yoke 1; a septum coil 3 that is provided inside the gap portion 1s but at the outer side thereof in the radial direction (r) and in the circumferential direction of which, an electric current flows; a return coil 4 that is provided in such a way as to be at the inner side of the gap portion in the radial direction and to face the septum coil 3, and in which an electric current flows which has a direction opposite to that of the electric current that flows in the septum coil 3; and a vacuum duct 2 that is inserted between the septum coil 3 and the return coil 4 and extends in the circumferential direction. As a characteristic configuration according to the present invention, an auxiliary coil 5 for suppressing an unnecessary magnetic field (a skewed magnetic field) inside the vacuum duct 2 is provided between the septum coil 3 and the vacuum duct 2.

The heights of the septum coil 3 and the return coil 4 are set in such a way that in the axis direction (h: perpendicular to the radial direction r and the circumferential direction c), i.e., in the vertical direction at a time when the septum magnet is installed, they cover the rectangle opening of the yoke 1. The size of the auxiliary coil 5 is set in such a way that the height thereof is the same as that of the septum coil 3; the respective electric currents in the upper half portion thereof and the lower half portion thereof flow opposite to each other in the circumferential direction (c).

For the convenience of maintenance, the septum magnet 10 according to Embodiment 1 is configured in such a manner that as illustrated in FIG. 1(c), the yoke 1 can be separated into an upper yoke 1u and a lower yoke 1d with respect to the center thereof in the axis direction (h). The septum coil 3 can be separated into an upper septum coil 3u that is positioned and fixed on the upper yoke 1u and a lower septum coil 3d that is positioned and fixed on the lower yoke 1d. Similarly, the return coil 4 can also be separated into an upper return coil 4u that is positioned and fixed on the upper yoke 1u and a lower return coil 4d that is positioned and fixed on the lower yoke 1d. In contrast, the auxiliary coil 5 is formed of an upper auxiliary coil 5u that is provided at the upper side and in which an electric current flows in one direction and a lower auxiliary coil 5d that is provided at the lower side and in which an electric current flows in opposite direction to that of the electric current in the upper auxiliary coil 5u; however, both the upper auxiliary coil 5u and the lower auxiliary coil 5d are positioned and fixed on the vacuum duct 2.

As illustrated in FIG. 2, the septum coil 3 and the return coil 4 are connected in series with a driving power source 9M for the main coils; the auxiliary coil 5 is connected with a driving power source 9S for the auxiliary coil; the driving power sources 9M and 9S are connected with a control unit 60 that outputs control signals for controlling the respective drives thereof. As a result, an electric current having an adjusted and the same value can be made to flow in the septum coil 3 and the return coil 4, and an electric current having an otherwise adjusted value can be made to flow in the auxiliary coil 5.

Next, the operation will be explained with reference to FIGS. 3 through 5.

When the driving power source 9M is driven, the respective electric currents having directions opposite to each other in the circumferential direction flow in the septum coil 3 and the return coil 4, which are the main coils of the septum magnet 10. In this situation, for example, when an electric current having the negative direction (oriented to the front side of the paper) in the circumferential direction (c) flows in the septum coil 3 and an electric current having the positive direction (oriented to the rear side of the paper) in the circumferential direction (c) flows in the return coil 4, as illustrated in FIG. 3(a), a main magnetic field B downward in the vertical direction is generated, on a beam region referred as a mid-plane Pm situating in the middle in the vertical direction of the plane (r-h plane) perpendicular to the circumferential direction of the vacuum duct 2. Accordingly, because a particle beam traveling in the positive direction of the circumferential direction (c) in the vacuum duct 2 is deflected toward the septum coil 3 (in the positive direction of the direction (r)), it is moved from the vicinity of the vacuum duct 2 to the vicinity of the duct 11 (e.g., the circulation orbit of the accelerator). Alternatively, because a particle beam traveling in the negative direction of the direction (c) in the vacuum duct 11 is deflected toward the septum coil 4 (in the negative direction of the direction (r)), it is moved from the vicinity of the duct 11 (e.g., the circulation orbit of the accelerator) to the vicinity of the vacuum duct 2.

In this situation, when as described above, the yoke 1 can be separated into the upper yoke 1u and the lower yoke 1d, a horizontal-direction (direction r or c) installation error (misalignment) between the upper septum coil 3u and the lower septum coil 3d may be caused not only at a time when the initial installation is implemented but also each time the yoke 1 is opened or closed for maintenance. In this case, as illustrated in FIG. 3(b), a magnetic field Bw including a skewed magnetic field, which is an unnecessary magnetic-field component (in the direction r) other than the main magnetic field B (in the direction h), is generated on the mid-plane Pm. In this situation, as represented in FIG. 4(a), the nearer to the coil the position is, the higher the magnetic flux density becomes; therefore, as illustrated in FIG. 3(b), the near to the coil the position is, the more the amount of the magnetic field Bw is likely to become in which the absolute value of the skewed magnetic field component increases.

However, the septum magnet 10 according to Embodiment 1 can suppress the unnecessary magnetic field component by adjusting a current that flows in the auxiliary coil 5. The septum coil 3 and the return coil 4 that generate the main magnetic field B are arranged in such a way that as described above, coils having same height face each other with a constant spacing; the current that has flown in the septum coil 3 returns to the power source by way of the return coil 4. In contrast, the auxiliary coil 5 is formed in such a way that the respective currents that flow in the upper auxiliary coil and the lower auxiliary coil have the directions opposite to each other and have the same current value and in such a way that because the auxiliary coil 5 is positioned and fixed on the vacuum duct 2, not only there exists no positional difference between the upper auxiliary coil 5u and the lower auxiliary coil 5d, but also the overall height of the upper auxiliary coil 5u and the lower auxiliary coil 5d is the same as that of the septum coil 3. Accordingly, the direction of the magnetic field generated by the auxiliary coil 5 is perpendicular to the main magnetic field B. On top of that, as described above, there exists no positional difference between the upper auxiliary coil 5u and the lower auxiliary coil 5d, and the overall height of the upper and lower auxiliary coils is the same as that of the septum coil 3; therefore, the spatial dependence of the unnecessary magnetic field generated by the positional difference between the upper and lower coils 3u and 3d of the septum coil 3 can be approximated with the spatial dependence of the magnetic field generated by the auxiliary coil 5. Accordingly, as represented in FIG. 4 (b), by forming magnetic field distributions evenly in the upper and lower regions, regardless of the coordinates on the mid-plane Pm, the unnecessary magnetic field can be cancelled.

Here, the beam orbit in the vacuum duct 2 of the septum magnet 10 will be explained.

FIG. 5 represents the orbit of a particle beam in the range of 300 mm in the Z direction on an area, out of the cross section (X-Z plane: corresponding to r-c plane in the cylindrical coordinate system) perpendicular to the Z axis (corresponding to h in the cylindrical coordinate system) of the vacuum duct 2, that corresponds to a quarter of the cross section in the circumferential direction (c). In FIG. 5, the abscissa denotes the Z-direction length in an orthogonal coordinate system (X, Y, Z) and corresponds to the circumferential-direction length (c) in the cylindrical coordinate system utilized in FIGS. 1, 3, and 4; the ordinate denotes the X-direction length and corresponds to the radial-direction length (r). As represented in FIG. 5, a particle beam passes through the space between a duct aperture Dpi at the inner side of the vacuum duct 2 (at the side of the return coil 4) and a duct aperture DPx at the outer side of the vacuum duct 2 (at the side of the septum coil 3). The passing region is a predetermined-width region that ranges from an inner orbit Oi at the approximately middle portion of the duct aperture to an outer orbit Ox in the vicinity of the outer duct aperture DPx and is displaced toward the septum coil 3.

In other words, in the regions inside the vacuum duct 2, the unnecessary magnetic field Bw provides a larger effect to the region near to the septum coil 3 than to the region near to the return coil 4. Meanwhile, from the nature of the septum magnet 10, the size restriction on the septum coil 3 is severer than that on the return coil 4. Accordingly, it is easier to provide the auxiliary coil 5 in the vicinity of the return coil 4, the thickness restriction on which is looser than that on the septum coil 3 that needs to be finished thin. Alternatively, it is also conceivable to provide auxiliary coils on the top and bottom sides of the vacuum duct 2. However, because as represented in FIG. 4, the state of the unnecessary magnetic field changes depending on the region, the unnecessary magnetic field that provides an effect to a particle beam that has a width and passes through the vacuum duct 2 changes depending on the region. Therefore, even when the unnecessary magnetic field is simply suppressed in a narrow region where the mid-plane Pm exists, the effect of suppressing the effect of the unnecessary magnetic field is small; thus, the unnecessary magnetic field needs to be suppressed in all the passing regions of a particle beam.

Accordingly, as Embodiment 1, by providing the auxiliary coil 5 between the septum coil 3 and the vacuum duct 2, the spatial dependence of the unnecessary magnetic field is approximated with the spatial dependence of the magnetic field generated by the auxiliary coil 5 at least in the region where an effect is provided to the orbit, so that the unnecessary magnetic field Bw that provides an effect to the orbit control can efficiently be suppressed. It is difficult that the auxiliary coil 5 is formed tubular (hollow conductor), as the septum coil 3, in order to finish the auxiliary coil 5 thin and is cooled with water flowing therein. In that case, for example, the auxiliary coil 5 and the vacuum duct 2 may be adhered to each other in an electrically insulated manner so as to form a heat conductive path and to cool the auxiliary coil 5.

The foregoing unnecessary magnetic field becomes stronger as the positional difference between the upper and lower coils is larger. For example, in the case where the positional difference in the radial direction (r) between the upper and lower septum coils 3u and 3d (although the return coil 4 is also displaced, the septum coil is described because as described above, the problem is the positional difference between the upper and lower septum coils 3u and 3d) is 0.5 mm, the unnecessary magnetic field component is distributed in a range from the septum coil 3 to the center portion of the mid-plane Pm, as represented in FIG. 4. However, an electric current that is approximately one-twentieth of the main coil current, i.e., the electric current that flows in the septum coil 3 is made to flow in the auxiliary coil 5 configured as described above, so that a magnetic field having a spatial dependence similar to the spatial dependence of the unnecessary magnetic field is generated and hence the unnecessary magnetic field can be suppressed. Similarly, when the positional difference is 0.3 mm, an electric current that is approximately 1/65 of the electric current that flows in the septum coil 3 is made to flow in the auxiliary coil 5, so that a magnetic field having a spatial dependence similar to the spatial dependence of the unnecessary magnetic field is generated and hence the unnecessary magnetic field can be suppressed.

When as is the case with the septum coil 3 or the return coil 4, the upper and lower yokes 1u and 1d are selected as the positioning objects for the auxiliary coil 5, the distance between the septum coil 3 and the auxiliary coil 5 can be kept evenly at the upper and the lower side, regardless of the installation situation. However, as far as the objective of approximating the spatial dependence of the unnecessary magnetic field with the spatial dependence of the magnetic field generated by the auxiliary coil 5 is concerned, it is more important to reduce the positioning error between the upper and lower auxiliary coils 5u and 5d; therefore, it is desirable to select, as the positioning object, the vacuum duct 2, which is not separated into upper and lower portions, as described in Embodiment 1.

Next, the configuration of a particle beam therapy system having the septum magnet 10 according to Embodiment 1 of the present invention will be explained with reference to FIG. 6.

In FIG. 6, the particle beam therapy system is provided with a circular accelerator (simply referred to as an accelerator, hereinafter) 100, which is a synchrotron as the supply source of a particle beam; a transport system 30 that transports a particle beam supplied from the accelerator 100; an irradiation apparatus that irradiates a particle beam transported by the transport system 30 onto a patient K; and a treatment room 50 provided with the irradiation apparatus 40. The septum magnet 10 is provided in the accelerator 100, as an injector 10A for taking a particle beam ejected from a prestage accelerator 20 into the accelerator 100 and as an ejector 10B for ejecting a particle beam accelerated in the accelerator 100 into the transport system 30.

<Accelerator>

The accelerator 100 is provided with a vacuum duct 11 that serves as an orbit path through which a particle beam circulates; the injector 10 for injecting a particle beam supplied from the prestage accelerator 20 into a circular orbit; deflection electromagnets 13a, 13b, 13c, and 13d (collectively referred to as 13) for deflecting the orbit of a particle beam in such a way that the particle beam circulates along the circular orbit in the vacuum duct 11; convergence electromagnets 14a, 14b, 14c, and 14d (collectively referred to as 14) for converging a particle beam formed on the circular orbit not to diverge; a high-frequency wave acceleration cavity 15 that applies a high-frequency voltage, synchronized with a circulating particle beam, to the circulating particle beam so as to accelerate the particle beam; the ejector 10B for extracting from the accelerator 100 a particle beam accelerated in the accelerator 100 and ejecting the extracted particle beam into the transport system 30; and a six-pole electromagnet 17 that excites resonance in the circular orbit of a particle beam so as to eject a particle beam from the ejector 10B.

As is the case where the explanation about the drive of the septum magnet 10 has been made with reference to FIG. 2, there are provided unillustrated apparatuses, for controlling the constituent units, such as a deflection electromagnet control apparatus that is provided in the deflection electromagnet 13 and controls the excitation current for the deflection electromagnet 13, and a high-frequency wave source for supplying a high-frequency voltage to the high-frequency wave acceleration cavity 15 and a high-frequency wave control apparatus for controlling the high-frequency wave source, which are provided in the high-frequency wave acceleration cavity 15; in a control unit 60, there is provided an accelerator control apparatus that controls the whole accelerator 100 by controlling other components such as the deflection electromagnet control apparatus, the high-frequency wave control apparatus, and convergence electromagnet 14.

In FIG. 1, for the sake of simplicity, the prestage accelerator 20 is illustrated as if it is a single apparatus; however, in practice, the prestage accelerator 20 includes an ion source (ion beam generator) that generates a charged particle (ion) such as a proton or a carbon particle (heavy particle) and a linear accelerator system that performs initial acceleration of a generated charged particle. A charged particle injected from the prestage accelerator 20 into the accelerator 100 is accelerated in a high-frequency electric field up to 70% to 80% of the light velocity, as it is being bent by means of the magnets.

<Transport System>

The particle beam accelerated by the accelerator 100 is ejected into the transport system 30, which is referred to as an HEBT (High Energy Beam Transport) system. The transport system 30 is provided with a vacuum duct 31 that serves as a transport path for a particle beam; a switching electromagnet 32, which is a switching device for switching the beam orbits of a particle beam; and a deflection electromagnet 33 that deflects a particle beam at a predetermined angle. The particle beam that has been sufficiently energized by the accelerator 100, that is ejected from the ejector 10B, and that travels through the vacuum duct 31 is led to the irradiation apparatus 40 provided in a designated treatment room 50; changing a transport path (a transport path 30A for a treatment room 50A, a transport path 30B for a treatment room 50B, - - - , a transport path 30N for a treatment room 50N) of the particle beam by the switching electromagnet 32, as may be necessary.

<Irradiation Apparatus>

The irradiation apparatus 40 forms a particle beam supplied from the transport system 30 into an irradiation field conforming to the size or the depth of a diseased site of a patient as an irradiation subject and irradiates the particle beam onto the diseased site. There exist two or more methods of forming an irradiation field; for example, in the scanning irradiation method in which an irradiation field is formed by scanning a particle beam, the accuracy of the orbit path particularly at a time when the particle beam is injected provides a large effect to the accuracy of the irradiation field. Accordingly, because by utilizing the septum magnet 10 according to Embodiment 1, the effect of an unnecessary magnetic field is suppressed and hence a particle beam is supplied on the preset orbit, an irradiation field can be formed as per setting; thus, the effect provided to the peripheral tissues are minimized and hence an effective therapy can be performed.

<Treatment Room>

The treatment room 50 is a room where therapy is performed by practically irradiating a particle beam onto the patient K; basically, each treatment room has the foregoing irradiation apparatus. In FIG. 6, the treatment room 50A is exemplified by a rotating irradiation room (referred to also as a rotating gantry) where the whole system from the deflection electromagnet 33 to the irradiation apparatus 40A revolves around the patient K (treatment table) so that the irradiation angle of a particle beam for the patient K can freely be set. In general, for a single accelerator 100, there are provided two or more treatment rooms such as a horizontal irradiation room in which a particle beam is horizontally irradiated from an irradiation apparatus onto a patient who is fixed on a treatment table whose angle and position can freely be set and a treatment room of the other type.

<Control System>

In many cases, as the control system of a particle beam therapy system including a plurality of subsystems (the accelerator 100, the transport system 30, the irradiation apparatus 40 for each treatment room, and the like), there is utilized a hierarchical-type control system that includes a sub-controller that is dedicated to control of each subsystem and a main controller that conducts and controls the whole system. This configuration including a main controller and a sub-controller is adopted also in the control unit 60 of a particle beam therapy system according to Embodiment 1 of the present invention. The functions of the control system are shared in such a way that operations that can be controlled by the subsystem alone are controlled by the subsystem and operations to be controlled in a collaborative manner by a plurality of systems are controlled by the main controller.

Meanwhile, in general, as the control unit 60 of the particle beam therapy system, a workstation or a computer is utilized. Accordingly, because being realized by software or the like, the functions of main controller and the sub-controller of the control unit 60 do not necessarily fall into specific hardware. Thus, although in FIG. 1, these devices are collectively illustrated as the control unit 60, it does not mean that the control unit 60 exists as a piece of physically unified hardware.

How to control the value of an electric current that flows in the foregoing auxiliary coil 5 in such a particle beam therapy system will be explained with reference to the flowcharts represented in FIGS. 7 through 9.

At first, the positional difference of the septum coil 3 is not uniform in the cross section taken along the line A-A, the cross section taken along the line B-B, and the cross section taken along the line C-C illustrated in FIG. 1(a). However, the distortion of a beam profile at the downstream side of the septum magnet 10 is determined by the integration amount obtained by circumferentially integrating the respective unnecessary magnetic field components (skewed magnetic fields) in the cross sections. Therefore, as described below, the electric current that flows in the auxiliary coil 5 can be calculated as a value corresponding to the integration value of the difference amount. These control items are implemented through the foregoing control unit 60.

1st CONTROL EXAMPLE

In the first control example, the current value (the current value corresponding to the value of a current that flows in the septum coil 3; the same applies hereinafter) of the auxiliary coil is determined by monitoring a beam profile (beam width, positional displacement) at the downstream side. The first control example will be explained with reference to FIG. 7.

At first, as the beam profile of a downstream, the beam width or the positional displacement at the downstream side of the septum magnet 10 is measured (the step S10); then, the kick angle caused by a skewed magnetic field or the strength of the skewed magnetic field is calculated through a beam calculation, based on the measured beam profile of a downstream (the step S20).

Then, based on the result of an electromagnetic-field analysis or the result of the measurement of a magnetic field at a time when an electric current is actually applied to the auxiliary coil 5, the value (provisional value) of an electric current to be applied to the auxiliary coil 5 for cancelling the calculated kick angle or the skewed magnetic field is calculated (the step S30). The current value of the auxiliary coil 5 is adjusted to the calculated provisional value (the step S40).

While the electric current whose value has been adjusted to the provisional value is applied to the auxiliary coil 5, the beam profile of a downstream is measured (the step S50). In this situation, in the case where the amount of a variation in the setting value of the beam profile of a downstream is the same as or smaller than a reference value ("Y" in the step S60), the provisional value is adopted as the setting value, and then the first control is ended. In contrast, in the case where the amount of a variation in the setting value of the beam profile of a downstream exceeds the reference value ("N" in the step S60), the step S60 is followed by the step S20; then, the current value of the auxiliary coil 5 is adjusted again.

2nd CONTROL EXAMPLE

In the second control example, the component of a skewed magnetic field is measured by use of a magnetic-field sensor, and then the current value of the auxiliary coil 5 is determined based on the integral value in the circumferential direction. The second control example will be explained with reference to FIG. 8.

At first, by use of a magnetic-field sensor such as a hole device, the skewed magnetic field in the vacuum duct 2 is measured at several points in the circumferential direction (the step S12); then, the integration value is calculated from the measured skewed magnetic field or by use of a long pickup coil or the like (the step S22).

Then, based on the result of an electromagnetic-field analysis or the result of the measurement of a magnetic field at a time when an electric current is actually applied to the auxiliary coil 5, the value (provisional value) of an electric current to be applied to the auxiliary coil 5 for cancelling the skewed magnetic field is calculated (the step S30). The current value of the auxiliary coil 5 is adjusted to the calculated provisional value (the step S40).

While the electric current whose value has been adjusted to the provisional value is applied to the auxiliary coil 5, the skewed magnetic field is measured (the step S52). In this situation, in the case where the strength of the skewed magnetic field is the same as or smaller than a reference value ("Y" in the step S62), the provisional value is adopted as the setting value, and then the second control is ended. In contrast, in the case where the strength of the skewed magnetic field exceeds the reference value ("N" in the step S62), the step S62 is followed by the step S22; then, the current value of the auxiliary coil 5 is adjusted again.

3rd CONTROL EXAMPLE

In the third control example, the positional difference between the upper and lower coils is measured, and then the skewed magnetic field is calculated from the positional difference amount; then, the current value of the auxiliary coil 5 is determined based on the integral value in the circumferential direction. The third control example will be explained with reference to FIG. 9.

At first, the amount of the positional difference between the upper and lower coils is measured by use of an apparatus for measuring a position or a size such as a laser displacement meter (the step S13); then, the strength of the skewed magnetic field is calculated from the measured difference amount using electromagnetic-field analysis (the step S23).

Then, based on the result of an electromagnetic-field analysis or the result of the measurement of a magnetic field at a time when an electric current is actually applied to the auxiliary coil 5, the value (provisional value) of an electric current to be applied to the auxiliary coil 5 for cancelling the skewed magnetic field is calculated (the step S33). The current value of the auxiliary coil 5 is adjusted to the calculated provisional value (the step S40).

While the electric current whose value has been adjusted to the provisional value is applied to the auxiliary coil 5, the skewed magnetic field is measured (the step S53). In this situation, in the case where the strength of the skewed magnetic field is the same as or smaller than a reference value ("Y" in the step S63), the provisional value is adopted as the setting value, and then the third control is ended. In contrast, in the case where the strength of the skewed magnetic field exceeds the reference value ("N" in the step S63), the step S63 is followed by the step S33; then, the current value of the auxiliary coil 5 is adjusted again. In this case, in the step S33, the Correction amount for the current value is calculated again based on the strength of the skewed magnetic field at a time after the adjustment has been implemented.

With regard to the third adjustment example, a case where the skewed magnetic field is measured in the stop S53 has been explained; however, for example, it may be allowed that as is the case with the steps S50 and S60 in the first adjustment example, it is determined whether or not the provisional value is appropriate, by measuring the beam profile of a downstream.

These adjustments are implemented each time maintenance is performed and the value of the current applied to the auxiliary coil 5 vs. the value of the current applied to the septum coil 3 is, for example, tabulated and stored in the control unit 60, so that the effect of an unnecessary magnetic field is suppressed and hence a beam can be extracted onto an accurate orbit.

As described above, the septum magnet 10 according to Embodiment 1 includes the yoke 1 that is arc-shaped, that has a gap portion is opening at the outer circumference side thereof and extending in a circumferential direction (c), and that can be separated at the approximately center portion thereof in the axis direction (h); the septum coil 3 that is provided inside the gap portion 1s but at the outer side thereof in the radial direction (r) and in which an electric current flows in one direction in the circumferential direction; the return coil 4 that is provided in such a way as to be at the inner side of the gap portion 1s in the radial direction and to face the septum coil 3 with a predetermined distance, and in which an electric current flows in opposite direction to that of the electric current in the septum coil 3; and the vacuum duct 2 that is inserted between the septum coil 3 and the return coil 4. The septum coil 3 is formed in such a way as to be able to be separated into the upper portion 3u, which is the first portion, and the lower portion 3d, which is the second portion, in response to the separation of the yoke 1; and in a space between the septum coil 3 and the vacuum duct 2, there is provided the auxiliary coil 5, in the portions 5u and 5d of which, corresponding to the upper portions 3u and 3d of the septum coil 3, respectively, electric currents flow in opposite direction to each other in the circumferential direction. As a result, even when the positional difference between the upper and lower septum coils 3u and 3d is caused when installation or maintenance is implemented, the auxiliary coil 5 generates a magnetic field in a distribution same as that of a skewed magnetic field caused by the positional difference; thus, the skewed magnetic field can efficiently be suppressed. Therefore, a septum magnet and a particle beam therapy system can be obtained which enable maintenance thereof to be readily performed and which can accurately control the orbit of a particle beam.

In particular, the auxiliary coil 5 is formed in such a way that the dimension thereof in the axis direction (h) is equal to that of the septum coil 3; therefore, because the magnetic field to be generated can be made closer to the skewed magnetic field, the skewed magnetic field can more efficiently be suppressed.

Furthermore, the auxiliary coil 5 is integrated with the vacuum duct 2 and positioned on the vacuum duct 2; therefore, because there exists no positional difference between the upper and lower auxiliary coils 5u and 5d and hence the distribution of the magnetic field to be generated can be made further closer to that of the skewed magnetic field, the skewed magnetic field can more efficiently be suppressed.

Furthermore, the particle beam therapy system according to Embodiment 1 includes the accelerator 100 that utilizes the septum magnet 10 according to Embodiment 1 at least as the ejector 10B for a particle beam, the transport system 30 that transports a particle beam ejected from the ejector 10B, the irradiation apparatus 40 that forms a particle beam supplied through the transport system 30 into a predetermined irradiation field and irradiates the particle beam; therefore, because a particle beam having an accurate ejecting position and an accurate orbit can be supplied to the irradiation apparatus 40, irradiation can be implemented with an accurate irradiation field.

Description Of Reference Numerals

1: yoke (1u: upper yoke, 1d: lower yoke, 1s: gap portion)
2: vacuum duct
3: septum coil (3u: upper septum coil (1st portion), 3d: lower septum coil (2nd portion)
4: return coil (4u: upper return coil, 4d: lower return coil)
5: auxiliary coil (5u: upper auxiliary coil (portion corresponding to 1st portion), 5d: lower auxiliary coil (portion corresponding to 2nd portion)
6: magnetic shield
9: driving power source (9M: for main coil, 9S: for auxiliary coil)
10: septum magnet
11: duct (circular orbit path)
20: prestage accelerator
30: transport system
40: irradiation apparatus
50: treatment room
60: control unit
100: accelerator

The invention claimed is:

1. A septum magnet comprising:
a yoke that (i) is arc-shaped, (ii) defines a gap portion at an outer circumference side thereof and extending in a circumferential direction thereof, and (iii) is configured to be separated at approximately a center portion thereof in an axial direction;
a septum coil provided inside the gap portion but at an outer side thereof in a radial direction and in which an electric current flows in one direction in the circumferential direction;
a return coil, in which an electric current flows in an opposite direction to that of the electric current in the septum coil, provided inside the gap portion in such a way as to (i) be at the inner side thereof in the radial direction and (ii) face the septum coil with a predetermined distance; and
a vacuum duct provided within the gap portion such that it is inserted between the septum coil and the return coil, wherein
the septum coil is configured to be separated into a first portion and a second portion upon separation of the yoke, and
in a space between the septum coil and the vacuum duct, an auxiliary coil is provided in first and second portions in which electric currents flow in opposite directions to each other in the circumferential direction, wherein (i) the first portion of the auxiliary coil is positioned on and fixed to the vacuum duct such that it is between the first portion of the septum coil and the vacuum duct and (ii) the second portion of the auxiliary coil is positioned on and fixed to the vacuum duct such that it is between the second portion of the septum coil and the vacuum duct.

2. The septum magnet according to claim 1, wherein the auxiliary coil is formed in such a way that a dimension of the auxiliary coil in the axial direction, which is perpendicular to both the radial direction and the circumferential direction, is equal to that of the septum coil.

3. A particle beam therapy system comprising:
an accelerator that utilizes the septum magnet according to claim 1, as at least a particle beam ejector;
a transport system that transports a particle beam ejected from the ejector; and
an irradiation apparatus that forms a particle beam supplied through the transport system into a predetermined irradiation field and irradiates the particle beam.

4. A particle beam therapy system comprising:
an accelerator that utilizes the septum magnet according to claim 2, as at least a particle beam ejector;
a transport system that transports a particle beam ejected from the ejector; and
an irradiation apparatus that forms a particle beam supplied through the transport system into a predetermined irradiation field and irradiates the particle beam.

5. The septum magnet according to claim 1, further comprising:
a first power source for driving the septum coil and the return coil; and
a second power source, different from the first power source, for separately driving the auxiliary coil.

* * * * *